United States Patent [19]
Genet et al.

[11] Patent Number: 5,542,952
[45] Date of Patent: Aug. 6, 1996

[54] DYE COMPOSITION CONTAINING SULPHUR-CONTAINING P-PHENYLENEDIAMINES AND CORRESPONDING DYEING PROCESSES, NOVEL SULPHUR-CONTAINING P-PHENYLENEDIAMINES AND PROCESS FOR THE PREPARATION THEREOF

[75] Inventors: Alain Genet, Aulnay-sous-Bois; Alain Lagrance, Coupvry, both of France

[73] Assignee: L'Oreal, Paris, France

[21] Appl. No.: 352,058

[22] Filed: Nov. 30, 1994

[30]    Foreign Application Priority Data

Dec. 1, 1993 [FR] France ..................................... 93 14398

[51] Int. Cl.⁶ ....................................... A61K 7/13
[52] U.S. Cl. ..................... 8/410; 8/406; 8/407; 8/408; 8/411; 8/412; 8/416; 8/587
[58] Field of Search ............................. 8/405, 406, 407, 8/408, 410, 411, 412, 416, 587

[56]                  References Cited

U.S. PATENT DOCUMENTS

| | | | |
|---|---|---|---|
| 1,940,757 | 12/1933 | Lehmann | ..................................... 8/411 |
| 3,918,896 | 11/1975 | Kalopissis et al. | ........................ 8/408 |
| 4,137,310 | 1/1979 | Wang | ..................................... 424/204 |
| 4,239,708 | 12/1980 | Asato et al. | ............................. 260/926 |

FOREIGN PATENT DOCUMENTS

| | | |
|---|---|---|
| 0166155 | 1/1986 | European Pat. Off. . |
| 50461 | 8/1967 | Luxembourg . |
| 9318739 | 9/1993 | WIPO . |
| 9316990 | 9/1993 | WIPO . |

*Primary Examiner*—Paul Lieberman
*Assistant Examiner*—Caroline L. Dusheck
*Attorney, Agent, or Firm*—Cushman Darby & Cushman, L.L.P.

[57]                  ABSTRACT

The present invention provides keratin fiber dyeing compositions containing sulfur-containing p-phenylenediamines and methods for their use.

13 Claims, No Drawings

DYE COMPOSITION CONTAINING SULPHUR-CONTAINING P-PHENYLENEDIAMINES AND CORRESPONDING DYEING PROCESSES, NOVEL SULPHUR-CONTAINING P-PHENYLENEDIAMINES AND PROCESS FOR THE PREPARATION THEREOF

Dye composition containing sulphur-containing p-phenylenediamines and corresponding dyeing processes, novel sulphur-containing p-phenylenediamines and process for the preparation thereof.

The invention relates to the field of the oxidation dyeing of keratin fibres, and more particularly to dye compositions containing sulphur-containing p-phenylenediamines, as well as to dyeing processes which use them.

It is known that p-phenylenediamines play a very important role in the oxidation dyeing of keratin fibres and in particular of the hair, whether they are used alone or in combination with coupling agents such as m-phenylenediamines, m-aminophenols, m-diphenols or phenols.

In order that an oxidation dye, and in particular a p-phenylenediamine, may be selected for dyeing hair, it has to display a good level of harmlessness when applied in a hair dye, and the shades imparted to the hair also have to be stable with time and, in particular, resistant to light, to inclement weather, to washing and to the various treatments to which hair may be subjected, for the duration which normally separates two successive hair colouring sessions.

The Applicant has discovered, surprisingly, that a particular family of sulphur-containing p-phenylenediamines simultaneously displays, on the one hand, a better level of harmlessness with regard to its application in dyeing keratin fibres and in particular hair, and, on the other hand, greater stability of the shades obtained with time, in particular good stability to inclement weather, to light, to washing and to the various treatments to which hair may be subjected, compared with the corresponding alkoxylated p-phenylenediamines.

The subject of the present invention is thus the dye composition containing at least one p-phenylenediamine from this family.

Another subject of the invention is a process for dyeing keratin fibres, and in particular human hair, using these p-phenylenediamines.

Another subject of the invention consists of novel sulphur-containing p-phenylenediamines belonging to this family, and to the process for the preparation thereof.

Finally, the invention relates to the novel p-nitroanilines used in the synthesis of the abovementioned p-phenylenediamines, and to the use thereof in the direct dyeing of the hair.

Other subjects of the invention will appear on reading the description and the examples which follow.

The compositions for dyeing keratin fibres, and in particular for human hair, in accordance with the invention, contain, in a medium which is suitable for dyeing, at least one compound of formula (I) or a corresponding acid salt in amounts which are effective for dyeing.

The compounds used in the compositions according to the invention correspond to the formula (I):

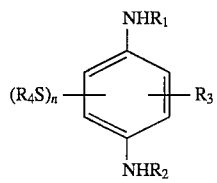

in which:
$R_1$ and $R_2$, which may be identical or different, represent a hydrogen atom, a $C_1$–$C_4$ alkyl radical, a $C_1$–$C_4$ hydroxyalkyl radical, a $C_2$–$C_4$ polyhydroxyalkyl radical or a $C_1$–$C_4$ aminoalkyl radical;

$R_3$ represents a hydrogen or halogen atom or a $C_1$–$C_4$ alkyl radical;

$R_4$ represents a $C_1$–$C_4$ alkyl radical, a $C_1$–$C_4$ hydroxyalkyl radical, a $C_2$–$C_4$ polyhydroxyalkyl radical, a $C_1$–$C_4$ acetylaminoalkyl radical, a $C_1$–$C_4$ aminoalkyl radical or a $C_1$–$C_4$ dialkylaminoalkyl radical which is optionally quaternized;

n is equal to 1 or 2; and when n=2, the groups —$SR_4$ are in a meta position relative to each other and $R_3$=H;

and when n=1 and $R_3$ is other than hydrogen, it is then in the position para to the —$SR_4$ group.

Among the compounds of formula (I), there may be mentioned:
2-acetylaminoethylthio-p-phenylenediamine,
2-methylthio-5-methyl-p-phenylenediamine,
2,6-dimethylthio-p-phenylenediamine,
2-ethylthio-1-N-(β-hydroxyethyl)-p-phenylenediamine,
3-ethylthio-1-N-(β-hydroxyethyl)-p-phenylenediamine
2-(β-hydroxyethylthio)-p-phenylenediamine,
2-methylthio-p-phenylenediamine,
2-ethylthio-p-phenylenediamine,
2-methylthio-5-chloro-p-phenylenediamine,
as well a the addition salts thereof with an acid.

A very particularly preferred compound is 2-methylthio-p-phenylenediamine dihydrochloride.

The compounds of formula (I) are preferably used in the compositions of the invention at a concentration of between 0.02 and 6%, and preferably of between 0.15 and 5%, by weight relative to the total weight of the composition.

The pH of the dye composition according to the invention is between 8 and 11 and preferably between 9 and 11.

It is adjusted to the desired value using basifying agents which are well known in the state of the art, such as aqueous ammonia, alkali metal carbonates, alkanolamines such as mono-, di- and triethanolamines as well as the derivatives thereof, sodium hydroxide and potassium hydroxide.

The dye compositions according to the invention may contain one or more compounds of formula (I) . They may also contain other p-phenylenediamines which are different from those of formula (I), such as, for example, those of formula:

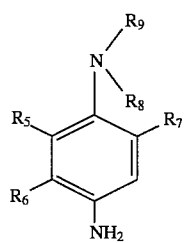

in which $R_5$, $R_6$ and $R_7$, which may be identical or different, represent a hydrogen or halogen atom, an alkyl radical, an alkoxy radical, a carboxyl or sulpho radical or a $C_1$–$C_4$ hydroxyalkyl radical;

$R_8$ and $R_9$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulphoalkyl, piperidinoalkyl or morpholinoalkyl radical, or a phenyl radical which is optionally para-substituted with an amino group; or alternatively $R_8$ and $R_9$ form, together with the nitrogen atom to which they are attached, a piperidino or morpholino heterocycle, with the proviso that $R_5$ or $R_7$ represents a hydrogen atom when $R_8$ and $R_9$ do not represent a hydrogen atom, as well as the salts of these compounds. These alkyl or alkoxy radicals preferably have 1 to 4 carbon atoms and especially denote methyl, ethyl, propyl, methoxy and ethoxy radicals.

Among the compounds of formula (II), p-phenylenediamine, p-toluylenediamine, methoxy-para-phenylenediamine, chloro-para-phenylenediamine, 2,3-dimethyl-paraphenylenediamine, 2,6-dimethyl-para-phenylenediamine, 2,6-diethyl-para-phenylenediamine, 2,5-dimethyl-paraphenylenediamine, 2-methyl-5-methoxy-para-phenylenediamine, 2,6-dimethyl-5-methoxy-para-phenylenediamine, N,N-dimethyl-para-phenylenediamine, N,N-diethyl-paraphenylenediamine, N,N-dipropyl-para-phenylenediamine, 3-methyl-4-amino-N,N-diethylaniline, N,N-di(β-hydroxyethyl)-para-phenylenediamine, 3-methyl-4-amino-N,N-di(β-hydroxyethyl)aniline, 3-chloro-4-amino-N,N-di (β-hydroxyethyl)aniline, 4-amino-N-ethyl-N-(carbamoylmethyl)aniline, 3-methyl-4-amino-N-ethyl-N-(carbamoylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl) aniline, 4-amino-N-(β-methoxyethyl) aniline, 3-methyl- 4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4-aminophenyl)piperidine, 2-(β-hydroxyethyl)-paraphenylenediamine, fluoro-paraphenylenediamine, carboxyparaphenylenediamine, sulphopara-phenylenediamine, 2-isopropyl-paraphenylenediamine, 2-n-propyl-paraphenylenediamine, hydroxy-2-n-propyl-para-phenylenediamine, 2 -hydroxymethyl-para-phenylenediamine, N,N-dimethyl-3-methyl-para-phenylenediamine, N-ethyl-N-(β-hydroxyethyl) -paraphenylenediamine, N-(dihydroxypropyl)-paraphenylenediamine, N-4-aminophenyl-paraphenylenediamine and N-phenyl-paraphenylenediamine may more particularly be mentioned.

These p-phenylenediamines may be used either in free base form or in the form of salts such as the hydrochloride, hydrobromide or sulphate.

The dye compositions according to the invention may also contain p-aminophenols such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 3-(β-hydroxyethoxy)- 4-aminophenol2-aminomethyl-4-aminophenol, 2-(β-hydroxyethylaminomethyl)-4-aminophenol, and those of formula (III) below:

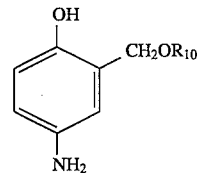

(III)

in which $R_{10}$ represents a $C_1$–$C_6$ alkyl radical, a $C_1$–$C_6$ hydroxyalkyl radical, a $C_2$–$C_6$ polyhydroxyalkyl radical, a $C_1$–$C_6$ haloalkyl radical, a $C_2$–$C_4$ aminoalkyl radical, or a $C_2$–$C_4$ aminoalkyl radical in which the amine may be mono-substituted or disubstituted with a $C_1$–$C_4$ alkyl group or substituted with a $C_3$–$C_4$ dihydroxyalkyl group, as well as the salts thereof.

Among these compounds of formula (III), there may in particular be mentioned:
2-methoxymethyl-4-aminophenol,
2-ethoxymethyl-4-aminophenol,
2-n-propyloxymethyl-4-aminophenol,
2-isopropyloxymethyl-4-aminophenol,
2-(β-hydroxyethoxy)methyl-4-aminophenol,
2-(2,2,2-trifluoroethoxymethyl-4-aminophenol,
as well as the salts thereof.

The dye compositions according to the invention may also contain so-called "double" bases, which are bisphenylalkylenediamines corresponding to the formula:

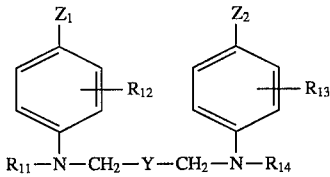

(IV)

in which:

$Z_1$ and $Z_2$, which may be identical or different, represent hydroxyl groups or groups $NHR_{15}$ where $R_{15}$ denotes a hydrogen atom or a lower alkyl radical;

$R_{12}$ and $R_{13}$, which may be identical or different, represent hydrogen atoms or halogen atoms or alkyl radicals;

$R_{11}$ and $R_{14}$, which may be identical or different, represent a hydrogen atom or an alkyl or hydroxyalkyl radical, or an aminoalkyl radical in which the amino residue may be substituted;

Y represents a radical taken from the group consisting of the following radicals:

$$-(CH_2)_n-, \quad -(CH_2)_m-O-(CH_2)_m-,$$
$$-(CH_2)_q-CHOH-(CH_2)_q-,$$
$$-(CH_2)_p-\underset{\underset{CH_3}{|}}{N}-(CH_2)_p-;$$

in which n is an integer between 0 and 8 and m, q and p are integers between 0 and 4, which base may also be provided in the form of the addition salts thereof with acids.

The alkyl or alkoxy radicals indicated above preferably denote a group having 1 to 4 carbon atoms and especially methyl, ethyl, propyl, methoxy and ethoxy.

Among the compounds of formula (IV), N,N'-bis(β-hydroxyethyl)-N,N'-bis( 4-aminophenyl)-1,3-diamino-2-propanol, N,N'-bis(β-hydroxyethyl)-N,N'-bis( 4-aminophenyl)ethylenediamine, N,N'-bis (4-aminophenyl)tetramethylenediamine, N,N'-bis(β-hydroxyethyl)-N,N'-bis(4-aminophenyl)tetramethylenediamne, N,N'-bis(4-methyl-aminophenyl)tetramethylenediamine and N,N'-bis(ethyl)-N,N'-bis(4-amino-3-methylphenyl)ethylenediamine may be mentioned.

The dye compositions according to the invention may also contain ortho-phenylenediamines and orthoaminophenols optionally containing substitutions on the ring or on amine functions.

Among the ortho-aminophenols, ortho-aminophenol, 6-methyl-1-hydroxy-2-aminobenzene, 4-methyl-1-amino-2-hydroxybenzene and 4-acetylamino-1-amino-2-hydroxybenzene may more particularly be mentioned, as well as the acid salts of these compounds.

The dye compositions which form the subject of the present invention generally contain, in combination with the "para" precursors consisting of the compounds of formula (I) and optionally with other oxidation dye precursors of para and/or ortho type, coupling agents which give dyes by oxidative coupling with these precursors.

The dyes are, in particular, indoanilines, indamines or indophenols of various shades, which contribute towards modifying and enriching with glints the "background" colorations imparted to the hair by the products of condensation of the "para" precursors with themselves.

The coupling agents used, generally in combination with the compounds of formula (I), in the dye compositions according to the invention are preferably chosen from meta-diphenols, meta-aminophenols, metaphenylenediamines, metal-acylaminophenols, metaureidophenols, meta-carbalkoxyaminophenols, α-naphthol, heterocyclic coupling agents, coupling agents possessing an active methylene group such as β-keto compounds, and pyrazolones.

Among the meta-diphenols, there may be mentioned: resorcine, 2-methylresorcine, 5-methylresorcine, 2-chlororesorcinol, resorcine monomethyl ether, 2,4-dihydroxyphenoxyethanol, 2,4-dihydroxyanisole, and the salts thereof. When combined with the compounds of formula (I), these compounds lead to beige-grey shades, via oxidative coupling.

Among the meta-aminophenols, there may be mentioned meta-aminophenol, 2-methyl-5-aminophenol, 2-methyl-5-N-(β-hydroxyethyl)aminophenol, 2-methyl- 5-N-(β-mesylaminoethyl)aminophenol, 2,6-dimethyl-3-aminophenol, 2-hydroxy-4-N-(β-hydroxyethyl)aminoanisole, 2-chloro-6-methyl-3-eminophenol, 2-methyl-3-aminophenol, 3-diethylaminophenol, 1-hydroxy-2,4-dichloro-3-aminobenzene, 4-chloro-6-methyl-3-eminophenol, 6-chloro-3-trifluoroethylaminophenol, and the salts thereof. When used with the compounds of formula (I), these coupling agents lead via oxidative coupling to purple shades.

Among the meta-phenylenediamines, there may be mentioned those which correspond to the formula:

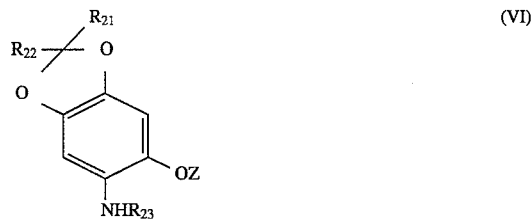

in which:

$R_{16}$ and $R_{17}$ denote, independently of each other, a hydrogen atom or a $C_1$–$C_4$ alkyl or $C_1$–$C_4$ hydroxyalkyl group;

$R_{18}$ denotes a hydrogen atom or a $C_1$–$C_4$ alkyl or alkoxy group;

$R_{19}$ denotes a hydrogen atom or a $C_1$–$C_4$ alkyl group, a $C_1$–$C_4$ hydroxyalkoxy group or a $C_1$–$C_4$ alkoxy group;

$R_{20}$ denotes a hydrogen or halogen atom or a $C_1$–$C_4$ alkyl group, a $C_1$–$C_4$ alkoxy group, a $C_1$–$C_4$ hydroxyalkyl group, a $C_1$–$C_4$ hydroxyalkoxy group, a $C_2$–$C_4$ polyhydroxyalkoxy group, a $C_1$–$C_4$ carboxyalkoxy group, a $C_1$–$C_4$ 2',4'-diaminophenoxyalkoxy group or a $C_1$–$C_4$ aminoalkoxy group;

with the proviso that if $R_{20}$ denotes carboxyalkoxy or 2',4'-diaminophenoxyalkoxy, then $R_{16}$, $R_{17}$, $R_{18}$ and $R_{19}$ denote hydrogen, as well as the salts thereof.

Among these meta-phenylenediamines, there may be mentioned meta-phenylenediamine, 2,4-diaminophenoxyethanol, 2,4-diaminoanisole, 2,4-dimethoxy-1,3-diaminobenzene, 1,3,5-trimethoxy-2,4-diaminobenzene, [2-N-(β-hydroxyethyl)amino-4-amino]phenoxyethanol, 2-amino-4-N-(β-hydroxyethyl)aminoanisole, [4-N-(β-hydroxyethyl)amino- 2-amino]phenoxyethanol, 4,6-bis(β-hydroxyethoxy)-1,3-diaminobenzene, (2,4-diamino)phenyl β,γ-dihydroxypropylether, (2,4-diamino)phenyl α,β-dihydroxylpropyl ether, 1-[2,4-diaminophenoxypropyloxy]-2,4-diaminobenzene, 2,4-diaminophenoxyacetic acid, 2,4-diaminophenoxyethylamine, 6-methoxy-3-hydroxyethylaminoaniline, 1-ethoxy-2-bis(β-hydroxyethyl)amino-4-aminobenzene, 4-methyl-6-ethoxy-1,3-diaminobenzene, and the salts thereof.

When used with the compounds of formula (I), these coupling agents give blue colours via oxidative coupling.

3,4-Methylenedioxyphenol, 3,4-methylenedioxyaniline, 2-bromo-4,5-methylenedioxyphenol, 2-chloro-4,5-methylenedioxyphenol, 6-aminobenzomorpholine and 6-hydroxybenzomorpholine may also be mentioned as coupling agents which may be used in the compositions of the invention.

As particularly advantageous coupling agents, there may finally be mentioned the heterocyclic compounds corresponding to the formula:

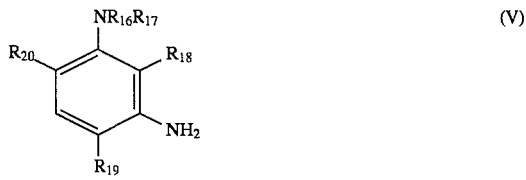

in which:

$R_{23}$ represents a hydrogen atom, a $C_1$–$C_4$ alkyl radical, a $C_2$–$C_4$ hydroxyalkyl radical, a $C_3$–$C_6$ polyhydroxyalkyl radical or a $C_2$–$C_6$ alkoxyalkyl radical;

Z, independently of $R_{23}$, represents a $C_1$ to $C_4$ alkyl radical, a $C_2$ to $C_4$ hydroxyalkyl radical, a $C_3$ to $C_6$ polyhydroxyalkyl radical, a $C_2$–$C_6$ alkoxyalkyl radical or a trifluoroethyl radical;

$R_{21}$ and $R_{22}$ denote, independently of each other, a hydrogen atom or a $C_1$ to $C_4$ alkyl radical, or one of the addition salts thereof with an inorganic acid, and in particular 4-amino-5-methoxy-1,2-methylenedioxybenzene, 4-(β-hydroxyethyl)amino-5-methoxy- 1,2-methylenedioxybenzene, 4-amino-5-(2,2,2-trifluoroethoxy)-1,2-methylenedioxybenzene, 4-methylamino-5-methoxy-1,2-methylenedioxybenzene, 4-amino-5-(β-hydroxyethoxy)-1,2-methylenedioxybenzene or 6-amino-5-methoxy-2-methyl-2-propyl-1,3-benzodioxole.

When used with the compounds of formula (I) along with 6-hydroxybenzomorpholine, these coupling agents give, via oxidative coupling, green shades which are particularly sought after in order to obtain matt shades for attenuating excessively red shades and for providing, if needed, a correction for the tendency which certain dyes have to redden with time.

Indole compounds such as 6-hydroxyindole, 7-hydroxyindole, 4-hydroxyindole, 7-aminoindole, 5,6-dihydroxyindole, and the derivatives thereof, as described in patents FR 2,636,236, FR 2,654,335, FR 2,654,336, FR 2,659,228, FR 2,664,304, FR 2,664,305 and FR 2,671,722, may also be used as coupling agents.

The compositions according to the invention may also contain direct dyes preferably chosen from azo dyes, anthraquinone dyes or nitro derivatives from the benzene series.

Addition of these direct dyes to the dye compositions according to the invention enables the colorations to be toned or to be enriched with glints.

All the oxidation dye precursors of para and/or ortho type, as well as the coupling agents used in the dye compositions in accordance with the invention, taken together, preferably represent from 0.1 to 7% by weight relative to the total weight of the said composition.

In their preferred embodiment, the dye compositions in accordance with the invention also contain anionic, cationic, nonionic or amphoteric surface-active agents or mixtures thereof. Among these surface-active agents, there may be mentioned alkylbenzenesulphonates, alkylnaphthalene-sulphonates, sulphates, ether sulphates and sulphonates of fatty alcohols, quaternary ammonium salts, such as trimethylcetylammonium bromide and cetylpyridinium bromide, fatty acid ethanolamides which are optionally oxyethylenated, polyglycerolated fatty alcohols, polyoxyethylenated or polyglycerolated alkylphenols, and polyoxyethylenated alkyl sulphates.

These surface-active agents are present in the compositions in accordance with the invention in amounts of between 0.5 and 55% by weight, and preferably of between 2 and 50% by weight, relative to the total weight of the composition.

These compositions may also contain organic solvents in order to dissolve components which would not be sufficiently water-soluble. Among these solvents, there may be mentioned by way of example $C_1$–$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether, and aromatic alcohols such as benzyl alcohol or phenoxyethanol, analogous products and mixtures thereof.

The solvents are preferably present in amounts of between 1 and 40% by weight, and in particular of between 2 and 30% by weight, relative to the total weight of the composition.

The thickening agents which may be added to the compositions in accordance with the invention may be chosen from sodium alginate, gum arabic, optionally crosslinked acrylic acid polymers, cellulose derivatives and heterobiopolysaccharides such as xanthan gum. Inorganic thickening agents such as bentonire may also be used.

These thickening agents are preferably present in amounts of between 0.1 and 5%, and in particular of between 0.2 and 3%, by weight relative to the total weight of the composition.

The antioxidants which may be present in the compositions are chosen in particular from sodium sulphite, thioglycolic acid, sodium bisulphite, dehydroascorbic acid, hydroquinone, 2-methylhydroquinone and homogentisic acid. These antioxidants are present in the composition in amounts of between 0.05 and 1.5% by weight relative to the total weight of the composition.

These compositions may also contain other cosmetically acceptable adjuvants, for example such as penetration agents, sequestering agents, fragrances, buffers, conditioning agents, preserving agents, etc.

The compositions in accordance with the invention may be provided in various forms, such as in the form of a liquid, a cream, gel or any other form which is suitable for dyeing keratin fibres and in particular human hair. These compositions may be packaged in aerosol cans in the presence of a propellant and may form foams.

The compounds of formula (I) in accordance with the invention are used for dyeing keratin fibres according to a process which comprises application of the compound of formula (I) to the said fibres, in the presence or absence of one or more coupling agents and/or oxidation dye precursors other than those of formula (I), and are developed by an oxidizing agent.

The dye compositions in accordance with the invention, containing at least one compound of formula (I) and optionally at least one coupling agent and/or at least one oxidation dye precursor other than those of formula (I), are used according to a process whereby the development is carried out by an oxidizing agent.

In accordance with this process, the dye composition described above is mixed, at the time of use, with an oxidizing solution in an amount which is sufficient to be able to develop a coloration, and the mixture obtained is then applied to the keratin fibres and in particular to human hair.

The pH of the composition applied to the hair preferably ranges between 3 and 11. It is adjusted to the desired value using basifying agents such as those described above or acidifying agents which are well known in the state of the art, such as inorganic or organic acids, for instance hydrochloric acid, tartaric acid, citric acid, phosphoric acid or sulphonic acid.

As oxidizing agent, the oxidizing solution may contain hydrogen peroxide or urea peroxide; persalts such as ammonium persulphate; organic peracids and the salts thereof, or alkali metal bromates. Hydrogen peroxide solution is preferably used.

The mixture obtained is applied to the hair and is left in place for 10 to 40 minutes, preferably for 15 to 30 minutes. The hair is then rinsed, washed with shampoo, rinsed again and dried.

The compound of formula (I) defined above may also be used in a multi-step process which consists, in one of the steps, in applying the compound of formula (I) and, in another step, in applying a dye composition containing at least one coupling agent and/or at least one other oxidation dye precursor which is different from those of formula (I).

The oxidizing agent may be introduced, just before application, into the composition which is applied in the second step or else may be applied to the keratin fibres themselves, in a third step, the application, pH, washing and drying conditions being identical to those indicated above.

The invention also relates to novel sulphur-containing p-phenylenediamines of the family of those corresponding to the formula (I).

These sulphur-containing p-phenylenediamines in accordance with the invention are essentially characterized in that they correspond to the formula:

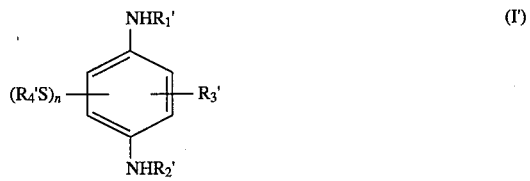

in which:

$R'_1$ and $R'_2$, which may be identical or different, represent a hydrogen atom, a $C_1$–$C_4$ alkyl radical, a $C_1$–$C_4$ hydroxyalkyl radical, a $C_2$–$C_4$ polyhydroxyalkyl radical or a $C_1$–$C_4$ aminoalkyl radical;

$R'_3$ represents a hydrogen or halogen atom or a $C_1$–$C_4$ alkyl radical;

$R'_4$ represents a $C_1$–$C_4$ alkyl radical, a $C_1$–$C_4$ hydroxyalkyl radical, a $C_2$–$C_4$ polyhydroxyalkyl radical, a $C_1$–$C_4$ acetylaminoalkyl radical, a $C_1$–$C_4$ aminoalkyl radical or a $C_1$–$C_4$ dialkylaminoalkyl radical which is optionally quaternized.

n is equal to 1 or 2; and when n=2, the groups —$SR_4$ are in a meta position relative to each other and $R_3$=H;

and when n=1 and $R_3$ is other than hydrogen, it is then in the position para to the —$SR_4$ group;

with the proviso that if $R'_1$ and $R'_2$ denote hydrogen, n=1 and $R'_4$ denotes a $C_1$–$C_4$ alkyl radical, then $R'_3$ cannot represent a hydrogen or halogen atom or the propyl or methyl radical; and with the proviso that when n=2 and $R'_1$, $R'_2$ and $R'_3$ denote a hydrogen atom, then the groups $R'_4$ cannot both simultaneously denote the methyl radical;

as well as the addition salts of these compounds with an acid. The salts are chosen in particular from hydrochlorides, sulphates, tartrates and other cosmetically acceptable salts.

Among the compounds of formula (I'), there may most particularly be mentioned:

2-acetylaminoethylthio-p-phenylenediamine,
2,6-dimethylthio-p-phenylenediamine,
2-β-hydroxyethylthio-p-phenylenediamine,
2-ethylthio-1-N-(β-hydroxyethyl)-p-phenylene-diamine,
3-ethylthio-1-N-(β-hydroxyethyl)-p-phenylene-diamine,
and the addition salts thereof with an acid.

The sulphur-containing p-phenylenediamines corresponding to the formula (I') may be prepared according to the process which consists essentially of the following steps:

1/ a halonitroaniline of formula (VII):

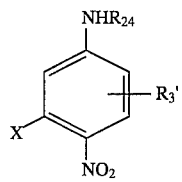

(VII)

which $R_{24}$ represents an acetyl radical or a hydrogen atom and $R'_3$ has the meaning defined in the formula (I'); X represents a halogen atom, is treated with a thiol of formula:

$ASR'_4$ (VIII)

in which $R'_4$ has the meaning defined in the formula (I') and A is a hydrogen or sodium atom, in order to obtain the p-nitroaniline of formula (IX):

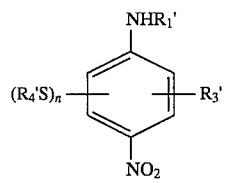

(IX)

2/ the $NO_2$ group of the compound of formula (IX) is reduced, either via reduction using hydrogen in the presence of a catalyst or via reduction on iron in acetic acid or on zinc in the presence of alcohol and ammonium chloride.

This process, in accordance with the invention, for preparing the compounds of formula (I') may be represented by the following reaction schemes.

Reaction Scheme No. 1

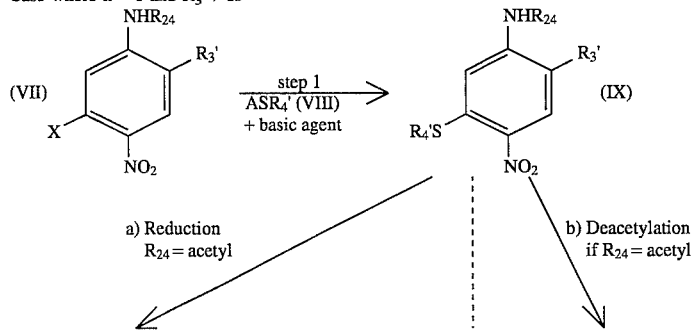

-continued
Reaction Scheme No. 1
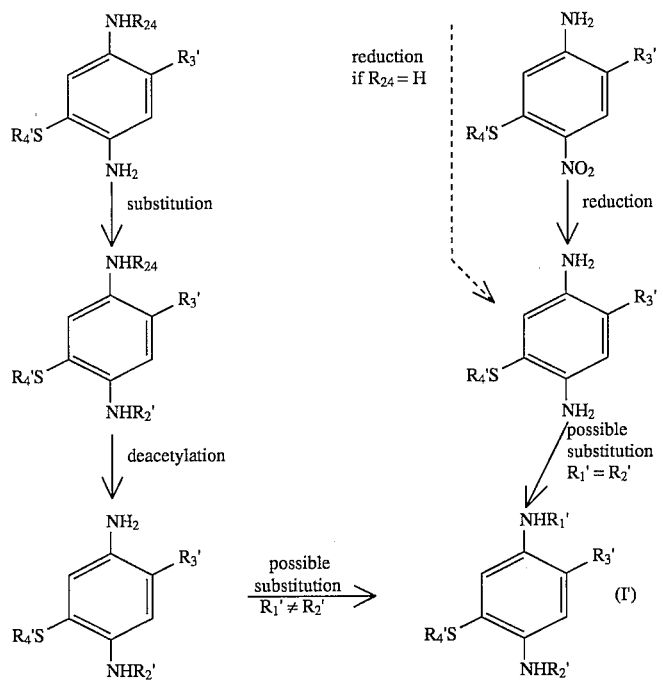
Reaction Scheme No. 2
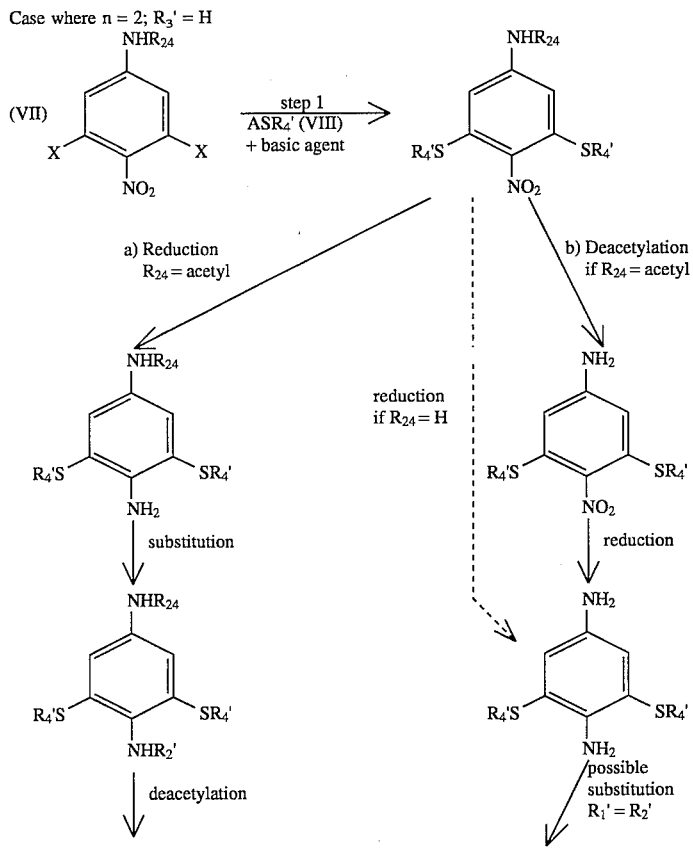

-continued
Reaction Scheme No. 2

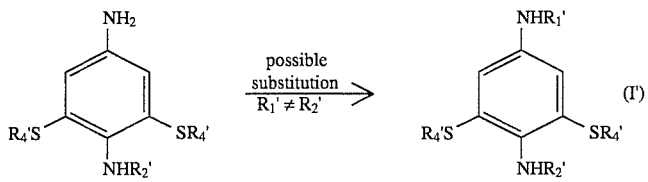

STEP 1

The p-nitroaniline of formula (IX) is prepared via the action of a thiol of formula $ASR'_4$ on a halonitroaniline of formula (VII), in which the radical $R'_3$ has the meaning defined above in the formula (I'). Substitution of the halo group or groups X is carried out in a solvent such as 1,2-dimethoxyethane, dimethylformamide, N-methylpyrrolidone, dioxane, dimethyl sulphoxide or hexamethylphosphotriamide. The reaction temperature is between room temperature and the reflux temperature of the reaction medium. The hydrohalic acid "traps" used are preferably chosen from sodium hydroxide, potassium hydroxide, triethylamine, sodium carbonate, potassium carbonate and calcium carbonate, as well as the sodium salts of the thiols used.

SUBSEQUENT STEPS a) If it is desired to obtain a compound of formula (I') in which the radical $R'_1$ is different from the radical $R'_2$, the process is then performed as follows:

reduction of the $NO_2$ group of the compound of formula (IX) in which $R_{24}$ is acetyl is carried out using hydrogen in the presence of a catalyst (Catalytic Hydrogenation Augustine R-L, Marcel DEKKER, Inc. NEW-YORK, 1965) or using iron in acetic acid or zinc in the presence of alcohol and ammonium chloride.

the amine located in the position para to the acetylamino group is then substituted according to standard methods for the substitution of aromatic amines, in order to obtain a group $—NHR'_2$, $R'_2$ having the meanings defined above in the formula (I');

the acetylamino group is then deacetylated according to standard methods for the deacetylation of aromatic amines, in order to obtain an amino group which is optionally substituted as indicated above, so as to obtain a compound of formula (I') in which the radicals $R'_1$ and $R'_2$ are different.

b) If it is desired to obtain a compound of formula (I') in which the radicals $R'_1$ and $R'_2$ are identical, the process is then performed as follows:

deacetylation of the group $—NHR_{24}$ is carried out as indicated above;

the $NO_2$ group is then reduced in order to obtain a compound of formula (I') in which $R'_1=R'_2=$hydrogen;

the aromatic amines are then optionally substituted, so as to obtain a compound of formula (I') in which $R'_1$ and $R'_2$ are identical but other than a hydrogen atom.

Another subject of the invention consists of the novel intermediate compounds corresponding to the formula:

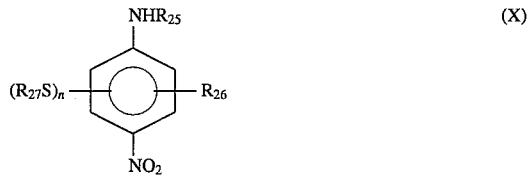

in which:

$R_{25}$ represents a hydrogen atom, a $C_1$–$C_4$ hydroxyalkyl radical or an acetyl radical;

$R_{26}$ represents hydrogen, halogen or a $C_1$–$C_4$ alkyl;

$R_{27}$ represents a $C_1$–$C_4$ alkyl radical, a $C_1$–$C_4$ acetylaminoalkyl radical or a $C_1$–$C_4$ hydroxyalkyl radical;

when n=2, the radicals $—SR_{27}$ are in a meta position relative to each other and each is ortho to the $—NO_2$ group, and $R_{26}$ denotes hydrogen;

when n=1 and $R_{26}$ is other than hydrogen, then the group $—SR_{27}$ is in a position para to the group $R_{26}$ and ortho to the $—NO_2$ group;

with the proviso that when n=1, the group $R_{25}$ is hydrogen and $R_{26}$ denotes hydrogen or methyl, then $R_{27}$ cannot denote methyl, for the preparation of the sulphur-containing p-phenylenediamines of formula (I').

Among these compounds, there may be mentioned:
2-methylthio-4-acetylaminonitrobenzene,
2-ethylthio-4-acetylaminonitrobenzene,
2-acetylaminoethylthio-4-acetylaminonitrobenzene,
2-ethylthio-4-aminonitrobenzene,
2-methylthio-4-amino-5-chloronitrobenzene,
2,6-dimethylthio-4-aminonitrobenzene,
2-ethylthio-4-N-(β-hydroxyethylamino)nitrobenzene,
2-(β-hydroxyethylthio)-4-acetylaminonitrobenzene,
2-(β-hydroxyethylthio)-4-aminonitrobenzene.

These compounds may also be used as dyes for the direct dyeing of the hair.

The examples which follow are intended to illustrate the invention.

PREPARATION EXAMPLES

EXAMPLE 1

SYNTHESIS OF 2-ETHYLTHIO-PARA-PHENYLENEDIAMINE DIHYDROCHLORIDE

1st Step: Preparation of 2-Ethylthio-4-Acetylaminonitrobenzene

To a suspension of 25.2 g (0.3 mol) of sodium thioethoxide in 220 ml of dimethoxyethane at room temperature are added, portionwise over 30 minutes with stirring, 46.2 g (0.216 mol) of 2-chloro-4-acetylaminonitrobenzene.

The reaction is exothermic; the temperature is maintained between 30° and 35° C. When the addition is complete, the stirring is continued for 1 hour, and the reaction medium (yellow suspension) is then poured into liters of ice-water.

The crystallized precipitate is drained off, reslurried several times in water until neutral, and then vacuum-dried over phosphorus pentoxide.

48.0 g (0.2 mol) of yellow crystals melting at 148° C. are obtained (recrystallization from boiling ethyl acetate), the elemental analysis of which, calculated for $C_{10}H_{12}N_2O_3S$, is:

| | % | | | | |
|---|---|---|---|---|---|
| | C | H | N | O | S |
| Calculated | 49.99 | 5.03 | 11.66 | 19.98 | 13.34 |
| Found | 49.82 | 5.08 | 11.64 | 20.02 | 13.16 |

2nd Step: Preparation of
2-Ethylthio-4-Aminonitrobenzene

Deacetylation of the compound obtained above in the first step is carried out by heating, for 10 minutes on a boiling water-bath, 24.0 g (0.1 mol) of this compound in a mixture of 50 ml of 36% concentrated hydrochloric acid and 15 ml of acetic acid. The reaction medium (suspension) is poured into 400 ml of ice-water and neutralized with aqueous ammonia containing 20% of $NH_3$.

The crystallized precipitate is drained, washed with water and recrystallized from 96° ethanol.

17.5 g of yellow crystals melting at 97° C. are obtained, the elemental analysis of which, calculated for $C_8H_{10}N_2O_2S$, is:

| | % | | | | |
|---|---|---|---|---|---|
| | C | H | N | O | S |
| Calculated | 48.47 | 5.08 | 14.13 | 16.14 | 16.17 |
| Found | 48.58 | 5.12 | 14.26 | 16.31 | 15.99 |

3rd Step: Reduction

To a suspension, heated to reflux, of 1.3 g of ammonium chloride and 34 g of finely-powdered zinc in 45 ml of 96° ethanol and 10 ml of water are added portionwise, so as to maintain the reflux without heating, 8.9 g of the nitro compound obtained above in the 2nd step. The reduction is exothermic. The colourless reaction medium is filtered while boiling. After cooling in a bath of ice, the filtrate is acidified with 17 ml of approximately 6N hydrochloric absolute ethanol.

The crystallized precipitate is drained, washed with ethyl ether and vacuum-dried at 40° C. over potassium hydroxide.

9.7 g of white crystals of 2-ethylthio-paraphenylenediamine dihydrochloride are obtained, melting with decomposition at 190°–193° C. and the elemental analysis of which, calculated for $C_8H_{12}N_2S0.2HCl$, is:

| | % | | | | |
|---|---|---|---|---|---|
| | C | H | N | S | Cl |
| Calculated | 39.84 | 5.85 | 11.61 | 13.29 | 29.40 |
| Found | 39.47 | 5.89 | 11.44 | 12.99 | 29.06 |

EXAMPLE 2

SYNTHESIS OF
2-ETHYLTHIO-1-N-(β-HYDROXYETHYL)-
PARAPHENYLENEDIAMINE
DIHYDROCHLORIDE

1st Step: Preparation of
2-Ethylthio-4-Acetylaminoaniline

According to the experimental procedure described in the 3rd step of Example 1, 22.8 g (0.094 mol) of 2-ethylthio-4-acetylaminonitrobenzene, obtained in the 1st step of Example 1, are reduced. The reaction medium is filtered while boiling. The filtrate is diluted with two volume of water, partially evaporated under reduced pressure to strip off the ethanol and extracted with ethyl acetate, the ethyl acetate phase is dried over sodium sulphate, filtered and evaporated to dryness.

An oily compound (19.0 g) is obtained, the elemental analysis of which, calculated for $C_{10}H_{14}N_2OS \cdot \frac{1}{4} H_2O$ is:

| | % | | | | |
|---|---|---|---|---|---|
| | C | H | N | O | S |
| Calculated | 55.92 | 6.80 | 13.04 | 9.31 | 14.93 |
| Found | 55.98 | 6.74 | 13.00 | 9.41 | 14.88 |

2nd Step: Preparation of
2-Ethylthio-4-Acetylamino-
1-(β-Chlorocarbethoxy)Aminobenzene To a suspension, heated on a boiling water-bath, of 18.9 g (0.09 mol) of the compound obtained in the above step and 9.1 g of calcium carbonate in 95 ml of dioxane, are added dropwise 9.9 ml (0.095 mol) of β-chloroethyl chloroformate. The heating is maintained for 1 hour and the suspension is then poured into 450 g of ice-water. After acidification with 36% hydrochloric acid, the crystallized precipitate is drained, reslurried in water and vacuum-dried over phosphorus pentoxide.

25.0 g of white crystals melting at 123° C. are obtained (recrystallized from refluxing ethyl acetate), the elemental analysis of which, calculated for $C_{13}H_{17}N_2O_3SCl$, is:

| | % | | | | | |
|---|---|---|---|---|---|---|
| | C | H | N | O | S | Cl |
| Calculated | 49.29 | 5.41 | 8.84 | 15.15 | 10.12 | 11.19 |
| Found | 49.27 | 5.43 | 8.61 | 15.29 | 9.98 | 11.47 |

3rd Step

The alkaline hydrolysis is performed by heating, on a boiling water-bath for 4 hours, the mixture of 24.0 g (0.075 mol) of the compound obtained in the above step, 70 ml of 96° alcohol, 35 ml of water and 70 ml of 10N caustic soda.

The reaction mixture (oil in suspension) is cooled in an ice bath, diluted with one volume of water, neutralized with acetic acid and partially evaporated under reduced pressure in order to remove the ethanol.

After extraction with ethyl ether, drying over sodium sulphate, filtering and evaporating to dryness, an oil is obtained which is purified by chromatography on silica gel (gradient of ethyl acetate and heptane). The purified oily compound is dissolved in absolute ethanol.

After adding 18 ml of approximately 6N hydrochloric absolute ethanol, the crystallized precipitate of 2-ethylthio-1-N-(β-hydroxyethyl)-para-phenylenediamine dihydrochloride is drained and is dried over potassium hydroxide at 30° C.

9.2 g of white crystals are obtained, melting with decomposition at 222°–223° C. and the elemental analysis of which, calculated for $C_{10}H_{16}N_2OS.2HCl$, is:

|  | % | | | | | |
|---|---|---|---|---|---|---|
|  | C | H | N | O | S | Cl |
| Calculated | 42.11 | 6.36 | 9.82 | 5.61 | 11.24 | 24.86 |
| Found | 42.08 | 6.38 | 9.85 | 5.64 | 11.49 | 24.63 |

EXAMPLE 3

SYNTHESIS OF 3-ETHYLTHIO-1-N-(β-HYDROXYETHYL)-PARAPHENYLENEDIAMINE DIHYDROCHLORIDE

1st Step: Preparation of 2-Ethylthio-4-N-(β-Chlorocarbethoxy)Aminonitrobenzene

This compound is prepared according to the experimental procedure described for the 2nd step of

EXAMPLE 2

Starting with 8.4 g (0.0423 tool) of 2-ethyl-thio-4-aminonitrobenzene (Example 1, 2nd step), 12.8 g of yellow crystals melting at 152° C. are obtained (recrystallized from ethyl acetate), the elemental analysis of which, calculated for $C_{11}H_{13}N_2O_4SCl$ is:

|  | % | | | | | |
|---|---|---|---|---|---|---|
|  | C | H | N | O | S | Cl |
| Calculated | 43.35 | 4.30 | 9.19 | 21.00 | 10.52 | 11.63 |
| Found | 43.48 | 4.46 | 9.01 | 20.87 | 10.54 | 11.58 |

2nd Step: Preparation of 2-Ethylthio-4-N-(β-Hydroxyethyl)Aminonitrobenzene

Alkaline hydrolysis of the compound obtained in the above step (11.7 g, 0.0384 mol) is performed over ¼ hour according to the experimental procedure described for the 3rd step of Example 2. The reaction medium is poured onto 300 g of ice-water. The crystallized precipitate is drained, re-slurried in water and recrystallized from 96° ethanol.

8.2 g of pale yellow crystals melting at 137° C. are obtained, the elemental analysis of which, calculated for $C_{10}H_{14}N_2O_3S$ is:

|  | % | | | | |
|---|---|---|---|---|---|
|  | C | H | N | O | S |
| Calculated | 49.57 | 5.82 | 11.56 | 19.81 | 13.23 |
| Found | 49.42 | 5.81 | 11.22 | 19.88 | 13.65 |

3rd Step

Reduction of the compound obtained in the above step (7.8 g, 0.034 mol) is performed according to the experimental procedure described in the 3rd step of Example 1.

5.8 g of white crystals of the dihydrochloride are obtained, melting with decomposition at 181°–183° C. and the elemental analysis of which, calculated for $C_{10}H_{16}N_2OS.2HCl$, is:

|  | % | | | | | |
|---|---|---|---|---|---|---|
|  | C | H | N | O | S | Cl |
| Calculated | 42.11 | 6.36 | 9.82 | 5.61 | 11.24 | 24.86 |
| Found | 41.98 | 6.39 | 9.77 | 5.50 | 11.26 | 24.80 |

EXAMPLE 4

SYNTHESIS OF 2-METHYLTHIO-PARA-PHENYLENEDIAMINE DIHYDROCHLORIDE

This compound is prepared according to the experimental procedure described for the 3rd step of Example 1, via reduction of 4.0 g (0.0217 mol) of 2-methylthio-4-aminonitrobenzene.

4.7 g of white crystals of the expected dihydrochloride are obtained, melting with decomposition at 210°–211° C. and the elemental analysis of which, calculated for $C_7H_{10}N_2S.2HCl$, is:

|  | % | | | | |
|---|---|---|---|---|---|
|  | C | H | N | S | Cl |
| Calculated | 37.01 | 5.32 | 12.33 | 14.12 | 31.21 |
| Found | 36.97 | 5.31 | 12.35 | 14.12 | 31.29 |

EXAMPLE 5

SYNTHESIS OF 2-ACETYLAMINOETHYLTHIO-PARA-PHENYLENEDIAMINE DIHYDROCHLORIDE

1st Step: Preparation of 2-Acetylaminoethylthio-4-Acetylaminonitrobenzene 8.3 g of powdered potassium hydroxide are dissolved in a solution of 29.8 g (0.25 mol) of N-(2-thioethyl)acetamide in 160 ml of dimethoxyethane heated to 40° C. After cooling to 30° C., 21.4 g (0.1 mol) of 2-chloro-4-acetylaminonitrobenzene are added portionwise over 30 minutes, while maintaining the temperature between 30° and 35° C., followed by heating for a further 30 minutes at 70° C. The yellow suspension is poured into 500 ml of ice-water. The crystallized precipitate is drained, re-slurried in water and dried at 40° C. over phosphorus pentoxide.

28.5 g of yellow crystals melting at 195° C. are obtained (recrystallized from 96° ethanol), the elemental analysis of which, calculated for $C_{12}H_{15}N_3O_4S$, is:

| | % | | | | |
|---|---|---|---|---|---|
| | C | H | N | O | S |
| Calculated | 48.48 | 5.09 | 14.13 | 21.52 | 10.78 |
| Found | 48.56 | 5.18 | 14.06 | 21.65 | 10.74 |

2nd Step: Preparation of 2-Acetylaminoethylthio-4-Acetylaminoaniline

The reduction is performed according to the experimental procedure described in the 1st step of Example 2, starting with 28.0 g (0,094 mol) of the compound obtained in the above step. White crystals (17.3 g) melting at 118° C. are obtained (recrystallized from acetonitrile), the elemental analysis of which, calculated for $C_{12}H_{17}N_3O_2S$, is:

| | % | | | | |
|---|---|---|---|---|---|
| | C | H | N | O | S |
| Calculated | 53.91 | 6.41 | 15.72 | 11.97 | 11.99 |
| Found | 53.48 | 6.47 | 15.60 | 12.56 | 11.85 |

3rd Step

The compound obtained in the 2nd step above (16.0 g, 0.06 mol) is stirred for 6 hours in 240 ml of normal aqueous hydrochloric acid solution. The solution is cooled in an ice-bath, neutralized with sodium hydroxide and extracted with ethyl acetate. The ethyl acetate phase is dried over sodium sulphate, filtered and evaporated to dryness under reduced pressure. The oil obtained is dissolved in 100 ml of absolute ethanol. This solution is acidified with 30 ml of approximately 6N hydrochloric absolute ethanol. The crystallized precipitate of the expected dihydrochloride is drained, washed with ethyl ether and vacuum-dried over potassium hydroxide.

6.2 g of white crystals are obtained, melting with decomposition at 198°–200° C. and the elemental analysis of which, calculated for $C_{10}H_{15}N_3OS.2HCl+¼ H_2O$, is:

| | % | | | | | |
|---|---|---|---|---|---|---|
| | C | H | N | O | S | Cl |
| Calculated | 39.67 | 5.83 | 13.88 | 6.61 | 10.59 | 23.42 |
| Found | 40.05 | 5.99 | 13.40 | 7.01 | 9.62 | 23.48 |

EXAMPLE 6

SYNTHESIS OF 2-METHYLTHIO-5-CHLORO-PARA-PHENYLENEDIAMINE DIHYDROCHLORIDE

1st Step: Preparation of 2-Methylthio-4-Amino-5-Chloronitrobenzene

To a suspension of 18.9 g (0.27 mol) of sodium thiomethoxide in 200 ml of dimethoxyethane, with stirring at room temperature, are added portionwise 41.4 g (0.2 mol) of 2,5-dichloro-4-aminonitrobenzene, allowing the temperature to rise to 50°–55° C. and maintaining this temperature for ½ hour after the addition is complete. The reaction medium is poured onto 2 liters of ice-water. The crystallized precipitate is drained, re-slurried in water and vacuum-dried at 40° C. over phosphorus pentoxide.

After recrystallization from 400 ml of refluxing ethyl acetate, 29.3 g of yellow crystals melting at 17.4° C. are obtained, the elemental analysis of which, calculated for $C_7H_7N_2O_2SCl$ is:

| | % | | | | | |
|---|---|---|---|---|---|---|
| | C | H | N | O | S | Cl |
| Calculated | 38.45 | 3.23 | 12.81 | 14.63 | 14.66 | 16.21 |
| Found | 38.52 | 3.17 | 12.71 | 14.92 | 14.43 | 16.15 |

2nd Step

The reduction is carried out according to the experimental procedure described for the 3rd step of Example 1. Starting with 10.9 g (0.05 mol) of the nitro compound prepared in the above step, 12.4 g of the dihydrochloride of the expected product are obtained, melting with decomposition at 245°–250° C. and the elemental analysis of which, calculated for $C_7H_9N_2SCl0.2HCl$, is:

| | % | | | | |
|---|---|---|---|---|---|
| | C | H | N | S | Cl |
| Calculated | 32.14 | 4.24 | 10.71 | 12.26 | 40.66 |
| Found | 32.24 | 4.29 | 10.81 | 12.19 | 40.68 |

EXAMPLE 7

SYNTHESIS OF 2-METHYLTHIO-5-METHYL-PARA-PHENYLENEDIAMINE DIHYDROCHLORIDE

According to the experimental procedure described for the 3rd step of Example 1, 9.9 g (0.05 mol) of 2-methylthio-4-amino-5-methylnitrobenzene are reduced in order to obtain 11.2 g of white crystals melting with decomposition at 196°–200° C., the elemental analysis of which, calculated for $C_8H_{12}N_2S0.2HCl$, is:

| | % | | | | |
|---|---|---|---|---|---|
| | C | H | N | S | Cl |
| Calculated | 39.84 | 5.85 | 11.61 | 13.29 | 29.40 |
| Found | 39.81 | 5.87 | 11.70 | 13.11 | 29.12 |

EXAMPLE 8

SYNTHESIS OF 2,6-DIMETHYLTHIO-PARA-PHENYLENEDIAMINE DIHYDROCHLORIDE

1st Step: Preparation of 2,6-Dimethylthio-4-Aminonitrobenzene

This compound is prepared according to the experimental procedure described for the 1st step of Example 6. Starting with 26.9 g (0.13 mol) of 2,6-dichloro-4-aminonitrobenzene and 0.35 mol of sodium thiomethoxide, 29.3 g of yellow crystals melting at 198° C. are obtained, the elemental analysis of which, calculated for $C_8H_{10}N_2O_2S_2$, is:

|  | % | | | | |
|---|---|---|---|---|---|
|  | C | H | N | O | S |
| Calculated | 41.72 | 4.38 | 12.16 | 13.89 | 27.84 |
| Found | 41.90 | 4.39 | 12.02 | 13.91 | 28.03 |

2nd Step

The reduction is performed according to the experimental procedure described in the 3rd step of Example 1. Starting with 10.1 g (0.044 mol) of the nitro compound prepared in the above step, 11.2 g of the expected dihydrochloride are obtained, the white crystals of which melt with decomposition at 216°–220° C. and the elemental analysis of which, calculated for $C_8H_{12}N_2S_2.2HCl$, is:

|  | % | | | | |
|---|---|---|---|---|---|
|  | C | H | N | S | Cl |
| Calculated | 35.17 | 5.16 | 10.25 | 23.47 | 25.95 |
| Found | 35.06 | 5.24 | 10.13 | 23.25 | 25.90 |

EXAMPLE 9

SYNTHESIS OF 2-(β-HYDROXYETHYLTHIO)-PARA-PHENYLENEDIAMINE DIHYDROCHLORIDE

1st Step: Preparation of 2-(β-Hydroxyethylthio)-4-Acetylaminonitrobenzene

This compound is prepared according to the experimental procedure described in the 1st step of Example 1, with two modifications: the trap is potassium carbonate and the reaction is carried out in refluxing dimethoxyethane.

Starting with 42.9 g (0.2 mol) of 2-chloro-4-acetylaminonitrobenzene and 23.4 g (0.3 mol) of 2-mercaptoethanol, pale yellow crystals (46.6 g) of the expected compound are obtained, the melting point of which is 174° C. (recrystallized from 96° ethanol) and the elemental analysis of which, calculated for $C_{10}H_{12}N_2O_4S.\frac{1}{2}CH_3CH_2OH$, is:

|  | % | | | | |
|---|---|---|---|---|---|
|  | C | H | N | O | S |
| Calculated | 47.30 | 5.41 | 10.03 | 25.78 | 11.48 |
| Found | 46.91 | 5.16 | 10.28 | 25.97 | 11.51 |

2nd Step: Preparation of 2-(β-Hydroxyethylthio)-4-Aminonitrobenzene

Deacetylation of the compound obtained above in the preceding step is carried out according to the experimental procedure described in the 2nd step of Example 1.

Starting with 45.6 g (0.18 mol) of the acetylated derivative, yellow crystals (16.1 g) melting at 146° C. are obtained, after recrystallization from ethyl acetate, the elemental analysis of which, calculated for $C_8H_{10}N_2O_3S$, is:

|  | % | | | | |
|---|---|---|---|---|---|
|  | C | H | N | O | S |
| Calculated | 44.85 | 4.70 | 13.08 | 22.40 | 14.97 |
| Found | 44.91 | 4.78 | 13.12 | 22.55 | 14.82 |

3rd Step

The reduction is performed according to the experimental procedure described for the 3rd step of Example 1.

Starting with 9.8 g (0.0457 mol) of the nitro compound obtained above in the preceding step, 9.6 g of the expected dihydrochloride are obtained, the white crystals of which melt with decomposition at 193°–195° C. and the elemental analysis of which, calculated for $C_8H_{12}N_2OS.2HCl+\frac{1}{4}H_2O$, is:

|  | % | | | | | |
|---|---|---|---|---|---|---|
|  | C | H | N | O | S | Cl |
| Calculated | 36.72 | 5.59 | 10.70 | 7.64 | 12.25 | 27.10 |
| Found | 36.77 | 5.54 | 10.59 | 7.86 | 11.99 | 27.33 |

DYEING EXAMPLES

Example 1

The following dye composition is prepared:

| | |
|---|---|
| $C_{16}$–$C_{18}$ cetyl/stearyl alcohol (50/50) sold under the name CIRE DE LANETTE O by the company HENKEL | 18 g |
| 2-Octyldodecanol | 3 g |
| Oxyethylenated $C_{16}$–$C_{18}$ cetyl/stearyl alcohol (35/65) containing 15 mol of ethylene oxide, sold under the name MERGITAL CS 15 by the company SINNOVA-HENKEL | 3 g |
| Ammonium lauryl sulphate containing 30% of AM | 12 g |
| Aqueous solution of a polymer formed from repeating units of formula: | 3 g |

$$\begin{array}{cc} CH_3 & CH_3 \\ | & | \\ -N^\oplus-(CH_2)_3-N^\oplus-(CH_2)_6- \\ | & | \\ CH_3 \quad Cl^- & CH_3 \quad Cl^- \end{array}$$

| | |
|---|---|
| containing 60% of AM | |
| Ammonium thiolactate containing 50% of thiolactic acid equivalent | 0.8 g |
| Aqueous ammonia containing 20% of $NH_3$ | 12 g |
| 2-Methylthio-para-phenylenediamine.2HCl | 0.3 g |
| Para-phenylenediamine | 0.4 g |
| Resorcinol | 0.6 g |
| Meta-aminophenol | 0.1 g |
| Ortho-aminophenol | 0.05 g |
| Para-aminophenol | 0.09 g |
| 6-Hydroxybenzomorpholine | 0.017 g |
| 2,4-Diaminophenoxyethanol.2HCl | 0.04 g |
| Demineralized water qs | 100 g |

This composition is diluted at the time of use with 1.5 times its weight of 20-volume hydrogen peroxide, the pH of which is 3.

The mixture thus prepared has a pH of 9.8 and is applied to natural hair containing 90% white hairs, for 30 minutes.

The hair is then rinsed, washed with shampoo and then rinsed again and dried.

The hair is dyed in a matt, slightly golden light chestnut shade.

Examples 2 to 19

The following dye compositions are prepared:

| | |
|---|---|
| Octyldodecanol sold under the name EUTANOL D by the company HENKEL | 8 g |
| Oleic acid | 20 g |
| Monoethanolamine lauryl ether sulphate sold under the name SIPON LM35 by the company HENKEL | 3 g |
| Ethyl alcohol | 10 g |
| Benzyl alcohol | 10 g |
| Cetyl/stearyl alcohol containing 33 mol of ethylene oxide, sold under the name SIMULSOL GS by the company SEPPIC | 2.4 g |
| Ethylenediaminetetraacetic acid | 0.2 g |
| Aqueous solution of a polymer formed from repeating units of formula: $$-\overset{\underset{\displaystyle CH_3}{\mid}}{\underset{\underset{\displaystyle CH_3}{\mid}}{N^{\oplus}}}-(CH_2)_3-\overset{\underset{\displaystyle CH_3}{\mid}}{\underset{\underset{\displaystyle CH_3}{\mid}}{N^{\oplus}}}-(CH_2)_6- \quad Cl^- \quad Cl^-$$ containing 60% of AM | 3.7 g |
| Monoethanolamine | 7.5 g |
| Linoleic acid diethanolamide sold under the name COMPERLAN F by the company HENKEL | 8 g |
| Aqueous ammonia containing 20% of $NH_3$ | 10.2 g |
| Sodium metabisulphite in aqueous solution at a concentration of 35% | 1.3 g |
| Hydroquinone | 0.15 g |
| 1-Phenyl-3-methyl-5-pyrazolone | 0.2 g |
| Dyes | X g |
| Demineralised water qs | 100 g |

MODE OF APPLICATION

The dye composition obtained is mixed weight for weight with 20-volume hydrogen peroxide, the pH of which is 3.

The mixture thus prepared is applied to grey hair containing 90% white hairs, which may or may not have been permanent-waved, for 30 minutes.

The hair is then rinsed, washed with shampoo and then rinsed again and dried.

The hair is dyed in the shades featured in the tables below:

| | ex. in g | | |
|---|---|---|---|
| DYE | 2 | 3 | 4 |
| 2-methylthio-p-phenylene-diamine.2HCl | 0.454 | 0.454 | 0.454 |
| 2-methyl-5-N-(β-hydroxyethyl)aminophenol | 0.334 | | |
| 2,4-diaminophenoxyethanol dihydrochloride | | 0.482 | |
| 6-hydroxyindole | | | 0.266 |
| pH of the mixture applied to the hair | 9.8 | 9.9 | 9.8 |
| Shade obtained | | | |
| *on natural grey hair containing 90% white hairs | mauve | | very light coppery-golden blond |
| *on permanent-waved grey hair containing 90% white hairs | | blue | |

| | in g | | | | | | | | |
|---|---|---|---|---|---|---|---|---|---|
| DYE | Ex. 5 | Ex. 6 | Ex. 7 | Ex. 8 | Ex. 9 | Ex. 10 | Ex. 11 | Ex. 12 | Ex. 13 |
| 3-ethylthio-1-N-(β-hydroxyethyl)-p-phenylenediamine dihydrochloride | 0.570 | 0.570 | 0.570 | | | | | | |
| 2-ethylthio-1-N-(β-hydroxyethyl)-p-phenylenediamine dihydrochloride | | | | 0.570 | 0.570 | | | | |
| 2-acetylaminoethylthio-p-phenylenediamine dihydrochloride | | | | | | 0.596 | 0.596 | 0.596 | 0.596 |
| 2-methyl-5-N-(β-hydroxyethyl)aminophenol | 0.334 | | | 0.334 | | 0.334 | | | |
| 2,4-diaminophenoxyethanol dihydrochloride | | 0.482 | | | 0.482 | | 0.482 | | |
| 2-(β-acetylaminoethylthio)-5-aminophenol | | | 0.453 | | | | | | 0.453 |
| resorcinol | | | | | | | | 0.220 | |
| pH of the mixture applied to the hair | 9.8 | 9.8 | 9.7 | 9.8 | 9.7 | 9.9 | 9.8 | 9.8 | 9.6 |
| Colour obtained on natural grey hair containing 90% white hairs | very violet light ashen blond | green-blue | green | iridescent very light blond | ashen-blue light blond | iridescent ashen light blond | blue | matt, slightly golden very light blond | very matt green |

| DYE | in g | | | | | |
|---|---|---|---|---|---|---|
| | Ex. 14 | Ex. 15 | Ex. 16 | Ex. 17 | Ex. 18 | Ex. 19 |
| 2-ethylthio-p-phenylenediamine dihydrochloride | 0.482 | 0.482 | | | | |
| 2,6-dimethylthio-p-phenylenediamine dihydrochloride | | | 0.546 | | | |
| 2-methylthio-5-methyl-p-phenylenediamine dihydrochloride | | | | 0.482 | 0.482 | |
| 2-methylthio-5-chloro-p-phenylenediamine dihydrochloride | | | | | | 0.523 |
| 2-methyl-5-N-(β-hydroxyethyl)aminophenol | 0.334 | | 0.334 | 0.334 | | 0.334 |
| 2,4-diaminophenoxyethanol dihydrochloride | | 0.482 | | | 0.482 | |
| pH of the mixture applied to the hair | 9.7 | 9.7 | 9.8 | 9.9 | 9.6 | 9.7 |
| Colour obtained on natural grey hair containing 90% white hairs | very pearlescent very light blond | matt ashen-bluish light blond | very light beige blond | iridescent very light blond | very matt light blond | very light beige blond |

EXAMPLES 20 to 38

The following dye compositions are prepared:

| | |
|---|---|
| Polyglycerolated oleyl alcohol containing 2 mol of glycerol | 4 g |
| Polyglycerolated oleyl alcohol containing 4 mol of glycerol (78% of AM) | 5.69 g AM |
| Oleic acid | 3 g |
| Oleyl amine containing 2 mol of ethylene oxide, sold under the name ETHOMEEN O12 by the company AKZO | 7 g |
| Diethylaminopropyl laurylaminosuccinamate sodium salt containing 55% of AM | 3 g AM |
| Oleyl alcohol | 5 g |
| Oleic acid diethanolamide | 12 g |
| Propylene glycol | 3.5 g |
| Ethyl alcohol | 7 g |
| Dipropylene glycol | 0.5 g |
| Propylene glycol monomethyl ether | 9 g |
| Sodium metabisulphite in aqueous solution containing 35% of AM | 1.3 g |
| Ammonium acetate | 0.8 g |
| Antioxidant, sequestering agent | qs |
| Fragrance, preserving agent | qs |
| Monoethanolamine | pH = 9.8 |
| Dyes | X g |
| Demineralized water | qs 100 g |

MODE OF APPLICATION

The composition obtained is mixed, weight for weight, with 20-volume hydrogen peroxide the pH of which is adjusted to between 1 and 1.5 with 2.5 g of orthophosphoric acid per 100 g of hydrogen peroxide.

The mixture is applied to natural grey hair containing 90% white hairs, for 30 minutes.

The hair is then rinsed, washed with shampoo, rinsed again and then dried.

The colours obtained are featured in the tables below.

| DYE | in g | | | | | | | | |
|---|---|---|---|---|---|---|---|---|---|
| | Ex. 20 | Ex. 21 | Ex. 22 | Ex. 23 | Ex. 24 | Ex. 25 | Ex. 26 | Ex. 27 | Ex. 28 |
| 2-methylthio-para-phenylenediamine dihydrochloride | 0.681 | 0.681 | 0.681 | | | | | | |
| 3-ethylthio-1-N-(β-hydroxyethyl)-p-phenylenediamine dihydrochloride | | | | 0.856 | 0.856 | 0.856 | | | |
| 2-ethylthio-1-N-(β-hydroxyethyl)-p-phenylenediamine dihydrochloride | | | | | | | 0.856 | 0.856 | 0.856 |
| 2-methyl-5-N-(β-hydroxyethyl)aminophenol | 0.501 | | | 0.501 | | | 0.501 | | |
| 2,4-diaminophenoxyethanol dihydrochloride | | 0.723 | | | 0.723 | | | 0.723 | |
| 2-(β-acetylaminoethylthio)-5-aminophenol | | | 0.679 | | | 0.679 | | | 0.679 |
| pH of the mixture applied to the hair | 6.7 | 6.7 | 6.6 | 6.7 | 6.6 | 6.8 | 6.8 | 6.7 | 6.7 |
| Coloration obtained | mauve | blue | violet | slightly iridescent very light ashen blond | matt blue | very matt very light ashen blond | slightly pearlescent very light blond | ashen blue light blond | iridescent very light ashen blond |

| DYE | Ex. 29 | Ex. 30 | Ex. 31 | Ex. 32 | Ex. 33 | Ex. 34 |
|---|---|---|---|---|---|---|
| 2-acetylaminoethylthio-para-phenylenediamine dihydrochloride | 0.895 | 0.895 | 0.895 | | | |
| 2-ethylthio-para-phenylenediamine dihydrochloride | | | | 0.724 | 0.724 | 0.724 |
| 2-methyl-5-N-(β-hydroxyethyl)aminophenol | 0.501 | | | 0.501 | | |
| 2,4-diaminophenoxyethanol dihydrochloride | | 0.723 | | | 0.723 | |
| 2-(β-acetylaminoethylthio)-5-aminophenol | | | | | | 0.679 |
| pH of the mixture applied to the hair | 6.7 | 6.7 | 6.6 | 6.7 | 6.6 | 6.8 |
| Coloration obtained | slightly pearlescent very light blond | ashen blue light blond | pearlescent ashen light blond | iridescent ashen light blond | ashen blue | slightly violet ashen blond |

| DYE | Ex. 35 | Ex. 36 | Ex. 37 | Ex. 38 |
|---|---|---|---|---|
| 2,6-dimethylthio-para-phenylenediamine dihydrochloride | 0.820 | | | |
| 2-methylthio-5-methyl-para-phenylenediamine dihydrochloride | | 0.724 | 0.724 | 0.724 |
| 2-methyl-5-N-(β-hydroxyethyl)aminophenol | | 0.501 | | |
| 2,4-diaminophenoxyethanol dihydrochloride | 0.723 | | 0.723 | |
| 2-(β-acetylaminoethylthio)-5-aminophenol | | | | 0.679 |
| pH of the mixture applied to the hair | 6.7 | 6.8 | 6.6 | 6.7 |
| Coloration obtained | matt dark blond | iridescent ashen light blond | ashen blue dark blond | ashen blond |

We claim:

1. Dye composition for keratin fibers which contains, in a medium which is suitable for dyeing, at least one compound of formula (I) in amounts which are effective for dyeing:

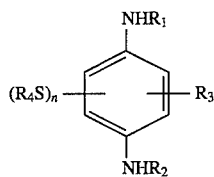

(I)

in which:

$R_1$ and $R_2$, which may be identical or different, represent a hydrogen atom, a $C_1$–$C_4$ alkyl radical, a $C_1$–$C_4$ hydroxyalkyl radical, a $C_2$–$C_4$ polyhydroxyalkyl radical, a $C_1$–$C_4$ acetylaminoalkyl radical or a $C_1$–$C_4$ aminoalkyl radical;

$R_3$ represents a hydrogen or a $C_1$–$C_4$ alkyl radical;

$R_4$ represents a $C_1$–$C_4$ alkyl radical, a $C_1$–$C_4$ hydroxyalkyl radical, a $C_2$–$C_4$ polyhydroxyalkyl radical, a $C_1$–$C_4$ aminoalkyl radical or a $C_1$–$C_4$ dialkylaminoalkyl radical which is optionally quaternized;

n is equal to 1 or 2; and when n=2, the groups —$SR_4$ are in a meta position relative to each other and $R_3$=H; and when n=1 and $R_3$ is other than hydrogen, $R_3$ is then in the position para to the —$SR_4$ group;

and the addition salts of said compounds with an acid, and at least one coupling agent.

2. Composition according to claim 1, wherein the compound of formula (I) is selected form the group consisting of:

2-acetylaminoethylthio-p-phenylenediamine, 2-methylthio-5-methyl-p-phenylenediamine, 2,6-dimethylthio-p-phenylenediamine, 2-ethylthio-1-N-(β-hydroxyethyl)-p-phenylenediamine, 3-ethylthio-1-N-(β-hydroxyethyl)-p-phenylenediamine, 2-(β-hydroxyethylthio)-p-phenylenediamine, 2-methylthio-p-phenylenediamine, 2-ethylthio-p-phenylenediamine, and the addition salts thereof with an acid.

3. Composition according to claim 2, wherein the compound of formula (I) is 2-methylthio-p-phenylenediamine dihydrochloride.

4. Composition according to claim 1 which contains 0.02 to 6% by weight, relative to the total weight of the composition, of compounds of formula (I).

5. Composition according to claim 1 further containing at least one para or ortho oxidation dye precursor chosen from p-phenylenediamines other than those of formula (I), p-aminophenols, bis-phenylalkylenediamines, o-phenylenediamines and o-aminophenols.

6. Composition according to claim 5 wherein said coupling agent is chosen from meta-diphenols, meta-aminophenols, meta-phenylenediamines, meta-acylaminophenols, meta-ureidophenols, meta-carbalkoxyaminophenols, α-naphthol, heterocyclic coupling agents, indole derivatives, and coupling agents possessing an active methylene group.

7. Composition according to claim 6 which further contains a direct dye chosen from azo dyes, anthraquinone dyes or nitroderivatives of the benzene series.

8. Composition according to claim 6 wherein said para or ortho oxidation dye precursors and coupling agents, taken together, are present in the composition in an amount of between 0.1 and 7% by weight relative to the total weight of the said composition.

9. Composition according to claim 1 which further contains at least one adjuvant chosen form cationic, anionic, non-ionic or amphoteric surface-active agents or mixtures thereof in amounts of between 0.5 and 55% by weight relative to the total weight of the composition; organic solvents in amounts of between 1 and 40% by weight relative to the total weight of the composition; thickening agents in amounts of between 0.1 and 5% by weight relative to the total weight of the composition; anti-oxidants in amounts of between 0.01 and 1.5% by weight relative to the total weight of the composition, penetration agents, sequestering agents, conditioning agents, preserving agents, fragrances and buffers.

10. Composition according to claim 1 which is provided in the form of a liquid, a cream, a gel or any other form which is suitable for dyeing, or may be packaged under pressure in an aerosol can in the presence of a propellant and may form foams.

11. A process for dyeing keratin fibers comprising developing a color wherein a dye composition containing, in a medium which is suitable for dyeing, at least one compound of formula (I):

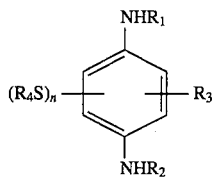

in which:

$R_1$ and $R_2$, which may be identical or different, represent a hydrogen atom, a $C_1$–$C_4$ alkyl radical, a $C_1$–$C_4$ hydroxyalkyl radical, a $C_2$–$C_4$ polyhydroxyalkyl radical or a $C_1$–$C_4$ aminoalkyl radical;

$R_3$ represents a hydrogen or a $C_1$–$C_4$ alkyl radical;

$R_4$ represents a $C_1$–$C_4$ alkyl radical, a $C_1$–$C_4$ hydroxyalkyl radical, a $C_2$–$C_4$ polyhydroxyalkyl radical; a $C_1$–$C_4$ acetylaminoalkyl radical, a $C_1$–$C_4$ aminoalkyl radical or a $C_1$–$C_4$ dialkylaminoalkyl radical which is optionally quaternized;

n is equal to 1 or 2; and when n=2, the groups —$SR_4$ are in a meta position relative to each other and $R_3$=H;

and when n=1 and $R_3$ is other than hydrogen, $R_3$ is then in the position para to the —$SR_4$ group;

and the addition salts of said at least one compound of formula (I) with an acid;

is applied to said fibers, said color being developed using an oxidizing agent which is present in an oxidizing solution in an amount which is sufficient to develop the color and is mixed at the time of use with a composition containing the compounds of formula (I); the pH of said composition applied to said keratin fibers being between 3 and 11.

12. The process according to claim 11 wherein said composition containing said compound of formula (I) further contains at least one coupling agent.

13. Process for dyeing keratin fibers comprising developing a color wherein a first composition containing, in a medium which is suitable for dyeing, at least one component (I):

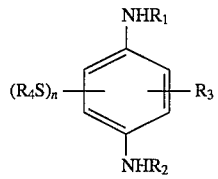

in which:

$R_1$ and $R_2$, which may be identical or different, represent a hydrogen atom, a $C_1$–$C_4$ alkyl radical, a $C_1$–$C_4$ hydroxyalkyl radical, a $C_2$–$C_4$ polyhydroxyalkyl radical or a $C_1$–$C_4$ aminoalkyl radical;

$R_3$ represents a hydrogen or a $C_1$–$C_4$ alkyl radical;

$R_4$ represents a $C_1$–$C_4$ alkyl radical, a $C_1$–$C_4$ hydroxyalkyl radical, a $C_2$–$C_4$ polyhydroxyalkyl radical, a $C_1$–$C_4$ acetylaminoalkyl radical, a $C_1$–$C_4$ aminoalkyl radical or a $C_2$–$C_4$ dialkylaminoalkyl radical which is optionally quaternized;

n is equal to 1 or 2; and when n=2, the groups —$SR_4$ are in a meta position relative to each other and $R_3$=H;

and when n=1 and $R_3$ is other than hydrogen, $R_3$ is then in the position para to the —$SR_4$ group;

and the addition salts of said compounds with an acid;

is applied to said fibers, this application being followed or preceded by application to said fibers of a second composition containing at least one of the group consisting of a coupling agent and an oxidation dye precursor which is different from those of formula (I);

said color being developed using an oxidizing agent which is applied either directly to said keratin fibers as a third composition or said oxidizing agent is introduced into said first or second composition, whichever is subsequently applied, just prior to said subsequent application.

* * * * *